United States Patent [19]

Wenke et al.

[11] Patent Number: 5,686,084
[45] Date of Patent: Nov. 11, 1997

[54] SYNTHESIS OF QUATERNARY MELANIN COMPOUNDS AND THEIR USE AS HAIR DYES OR FOR SKIN TREATMENT

[75] Inventors: Gottfried Wenke, Woodbridge, Conn.; Giuseppe Prota, Naples, Italy

[73] Assignee: Clairol Incorporated, New York, N.Y.

[21] Appl. No.: 568,057

[22] Filed: Dec. 6, 1995

[51] Int. Cl.$^6$ .................. A61K 7/48; A61K 7/13
[52] U.S. Cl. .............. 424/401; 424/59; 424/701; 424/706
[58] Field of Search ................. 424/401, 701, 424/706, 59; 548/492; 8/408

[56] References Cited

U.S. PATENT DOCUMENTS

| | | | |
|---|---|---|---|
| 3,194,734 | 7/1965 | Seemuller et al. | 167/88 |
| 4,804,385 | 2/1989 | Grollier et al. | 8/423 |
| 4,808,190 | 2/1989 | Grollier et al. | 8/423 |
| 4,888,027 | 12/1989 | Groller et al. | 8/423 |
| 4,968,497 | 11/1990 | Wolfram et al. | 424/59 |
| 5,006,331 | 4/1991 | Gaskin | 424/70 |
| 5,157,075 | 10/1992 | Kanai et al. | 525/54.1 |
| 5,188,844 | 2/1993 | Ahene et al. | 424/574 |
| 5,218,079 | 6/1993 | Pawelek et al. | 528/206 |
| 5,240,715 | 8/1993 | Ahene et al. | 424/574 |
| 5,273,550 | 12/1993 | Prota et al. | 8/405 |
| 5,346,509 | 9/1994 | Schultz et al. | 8/423 |

FOREIGN PATENT DOCUMENTS

| | | |
|---|---|---|
| 92 16189 | 10/1992 | WIPO . |
| 9425532 | 11/1994 | WIPO . |

OTHER PUBLICATIONS

Moncrieff, Manuf. Chemist, vol. XXI, No. 8, 330–4 (1950).
Prota, Medicinal Research Reviews, 8:525–56 (1988).

*Primary Examiner*—Jyothsan Venkat
*Attorney, Agent, or Firm*—Charles J. Zeller

[57] ABSTRACT

The specification describes water soluble, cationic products useful as hair colorants or for skin care obtained by oxidative polymerization of a 5,6-dihydroxyindole-2-quaternary amides or esters, as well as compositions containing the same, methods of using the same in compositions to color hair or treat skin and intermediates for producing the products.

19 Claims, No Drawings

SYNTHESIS OF QUATERNARY MELANIN COMPOUNDS AND THEIR USE AS HAIR DYES OR FOR SKIN TREATMENT

RELATED APPLICATIONS

Attention is directed to copending and concurrently filed patent application U.S. Ser. No. 08/568,056, filed Dec. 6, 1995, (Atty. Dkt. No. CP-1141), which describes melanin reaction products having properties similar to those of the products of this invention, but which are prepared from different starting materials.

BACKGROUND OF THE INVENTION

This invention relates to water soluble reaction products prepared by the oxidative polymerization of quaternized 5,6-dihydroxyindole-2-carboxylic acid amides or esters, to compositions containing such products, to methods of coloring hair or treating skin utilizing the compositions and to kits containing the compositions. More specifically, the invention relates to reaction products characterized by a quaternary nitrogen substituent and to intermediates useful for the preparation of the reaction products.

The reaction products of this invention are mixtures of many compounds formed by the oxidative polymerization of the aforementioned amide or ester derivatives of 5,6-dihydroxyindole-2-carboxylic acid (DHICA). The oxidative polymerization of DHICA and certain of its selected derivatives is described in commonly owned U.S. Pat. No. 5,346,509, the disclosure of which is incorporated herein by reference. The particular DHICA derivatives which are oxidatively polymerized to form the products of this invention are neither described nor suggested in the '509 patent.

To facilitate understanding of this invention, the following system will be employed in its description:

A: The oxidative polymerization products should be understood to be the reaction products of the invention. In addition to the term "reaction products of the invention", they are sometimes referred to as hair colorants, hair dyes or skin treatment products and, often, melanin like products of the invention.

B: The quaternized products formed by reaction of DHICA with selected quaternary compounds to be described more fully hereinafter are referred to as "intermediates" or as "intermediates of the invention".

C: Compositions of the invention may take several forms depending on their intended use. If the products of the invention are to be directly added to the hair or if they are to be formed on the hair by oxidative polymerization of intermediates of the invention, they will be aqueous. If they are to be employed for skin care they may be aqueous, non-aqueous or they may be mixtures of polar or non-polar organic solvents and may be either free flowing or viscous.

Notwithstanding their melanin-like properties, the reaction products of this invention are not true melanin derivatives. The reaction products of the present invention are mixtures of many compounds and thus cannot be precisely defined by a chemical formula. Accordingly they will be defined herein by their method of preparation. It is believed that the mixture of the compounds comprising the reaction products of this invention includes some dimers, trimers and tetramers of the intermediates. However, most species are oligomers and many are probably true polymers. Surprisingly, they have Substantially similar hair coloring and other properties compared to the melanin derivatives described in U.S. Ser. No. 08/568,056 (CP1141).

Naturally-occurring melanin is the pigment that gives hair its color. A general discussion of the properties and chemistry of melanins may be found in Prota, G., "Progress In The Chemistry of Melanins And Related Metabolites," *Med. Res. Reviews*, 8:525–56 (1988) and Moncrieff, R. W., *Manufacturing Chemist*, XXI, 8, 330–34 (August 1950). The gradual reduction of melanin formation with age causes hair to become gray.

Naturally-occurring melanin pigment itself is unacceptable for use in a hair dye composition because it is easily removed by rinsing or rubbing and leaves the hair feeling rough. One present method for coloring gray hair involves the use of naturally-occurring melanin precursors such as DHI that when combined with an oxidant, form useful melanin like pigments. See, for example, U.S. Pat. No. 3,194,734 (Seemuller et al.), U.S. Pat. No. 4,808,190 (Grollier et al.), and U.S. Pat. No. 4,888,027 (Grollier et al.). See also U.S. Pat. No. 5,346,509 (Schultz et al) which describes the conversion of DHICA to melanin like pigments.

The primary disadvantage is that the hair colors initially produced with melanin precursor dyes are undesirable achromatic colors (cold grays and blacks). Hair dyed with these colorants must undergo a second treatment step with an oxidant such as hydrogen peroxide to achieve natural chromatic colors (warm yellows, reds, and browns). See, for example, U.S. Pat. No. 3,194,734 (Seemuller et al.). In addition, melanin precursors are expensive and, because they are highly reactive, are difficult to work with. The use of melanin precursors also can result in undesirable scalp and skin staining.

Furthermore, because the pigments are formed from the melanin precursors in the hair shaft, the hair colors produced using the melanin precursors are permanent. The hair color must grow out to return to its original color. Often, consumers prefer to use a temporary hair color that will wash out after one or two shampoos.

The compositions described in PCT patent application S.N. US93/11174 filed Nov. 17, 1993 are useful as temporary hair colorants. These compositions contain melanin derivatives prepared by forming a complex between a water soluble anionic melanin with selected quaternary compounds, suitably alkyltrimonium halides, alkylalkonium halides or dialkyldimonium halides such as cetrimonium halide or stearalkonium halides. These complexes impart a temporary coloring to human hair when deposited thereon in aqueous compositions and thereafter dried. Although such compositions are acceptable to many consumers, they may not be acceptable to others because they wash off the hair too readily. Only rarely do they survive a single shampoo. In fact, normally they require a "leave on" treatment since they may be readily removed with even a water rinse.

The art has sought hair coloring compositions providing colors that are not as difficult to use as the melanin precursors or as permanent dyes, but are more permanent than the colors provided by the above described temporary hair colorants, i.e. dyes which will survive 4 to 6 shampoos or can be mixed with additional dyes in a shampoo base in order to freshen temporary hair colors. The hair colorants utilized in the compositions of this invention have these desirable properties. In that respect they are similar to the products of the above identified U.S. Ser. No. (CP-1141), but are prepared differently.

The compositions of this invention produce in a single treatment step semi-permanent natural-looking hair color that resist fading in sunlight, resist rub off and resist bleeding in contact with water. The compositions are inexpensive and simple to work with. It has surprisingly been found that aqueous compositions containing the reaction products of this invention will, when applied to hair, impart a semi-permanent color to the hair which will survive more than three shampoos without substantial loss of color characteristics. A particular advantage of the reaction products of this invention is that they can be combined with other hair colorants in a shampoo base to freshen the existing hair color whereby the hair color is renewed and retained for an appreciably further period of time. Another is that the reaction products can be used for simultaneous coloring and conditioning of hair.

The products of this invention are also useful for skin care. They may be used alone or, preferably, in conventional skin care compositions. When so employed, they function both as skin colorants to impart a tanned appearance to the treated skin and as sun screen agents to protect the skin from harmful infrared rays.

With both skin and hair, the products exhibit the other attributes of natural melanin, i.e., they are antioxidants and free radical scavengers and minimize hair damage caused by oxidants and free radicals often present in the hair after atmospheric exposure.

U.S. Pat. No. 5,006,331 (Gaskin) discloses the use of melanin compositions containing triethanolamine and ferric chloride. The resultant mixture of melanin, triethanolamine and ferric chloride is said to be useful for skin protection, for wound healing and for strengthening hair. An alternate composition contains trypsin in an alkaline medium. Melanin is present in the skin protectant compositions of Gaskin in an amount of from about 0.001 to about 0.09%, along with from about 0.0001% to about 0.27% ferric chloride, both being on a weight basis based on total weight. The skin protectant composition further contains up to about 5% by weight triethanolamine. While not providing a range of concentration for the amount of melanin hydrolysate for the hair protectant compositions according to her invention, Gaskin states at column 6, line 30 that it is present therein in an amount of only about 0.0015% by weight of the total composition. However, this level of Gaskin's melanin hydrolysate is wholly insufficient to impart a color to hair. Moreover, neither of Gaskin's methods provide a melanin material of a cationic character.

PCT Application WO 91/17738 discloses the use of soluble melanin derivatives in a process for producing lightly colored melanins that are aesthetically suitable for use in cosmetic compositions.

WO 94/25532 describes melanin linked to a lipid to form a lipomelanin and its use in a sunscreen product.

It is an object of this invention to provide an aqueous composition for semi-permanently coloring hair using water soluble melanin like products of the invention.

It is also an object of this invention to provide compositions that will produce a semi-permanent natural-looking hair color that resists fading in sunlight, will not rub off, and will not bleed when in contact with water.

It is further an object of this invention to provide inexpensive compositions for semi-permanently coloring hair using water soluble melanin like products of the invention.

It is also an object of this invention to provide compositions that are simple to work with for semi-permanently coloring hair using water soluble melanin like products of the invention.

It is also an object of this invention to provide a one-step process for semi-permanently coloring hair.

It is a further object of this invention to provide a compositions for simultaneously coloring and conditioning hair.

It is a still further object of this invention to provide compositions which when used with appropriate shampoos are useful for freshening hair colors.

It is a still further object of this invention to provide novel melanin like products of the invention and compositions thereof for skin care.

It is a still further object of the invention to provide novel intermediates useful for the production of melanin like products of the invention.

SUMMARY OF THE INVENTION

The presently preferred products of the invention are quaternary substituted esters or amides which may be obtained by oxidative polymerization of a novel intermediate of the invention represented by the formula:

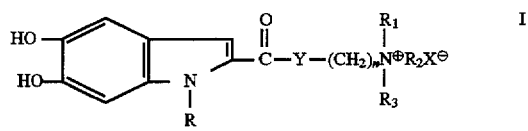

wherein

Y is —O— or

n is an integer from about 1 to about 20, preferably 6 to 15

R is hydrogen or alkyl containing from about 1 to about 6 carbon atoms $R_1$, $R_2$ and $R_3$ which may be the same or different are substituted or unsubstituted alkyl groups containing from about 1 to about 22 carbon atoms, preferably 12 to 16, and X is an anion.

The intermediates of this invention as will be recognized from the above formula are quaternary substituted esters or amides obtained by reacting DHICA or its N-substituted derivative with a quaternary ammonium compound. The quaternary reactant used to form an intermediate of this invention has at least one amino or hydroxyl group on one or more of the alkyl substituents which is free to react with the carboxyl group on the DHICA molecule to form the esters or amides. There may be other substituents on the alkyl groups of the quaternary reactant or on the linking alkylene group which may be chemically inert with respect to ester or amide formation, e.g., they may be halo, cyano, nitro or other groups, but which may be further reacted to produce desired colors.

Although the intermediates of the invention represented by the above formula are presently preferred, especially when they are prepared from quaternary compounds containing an unsubstituted amino alkylene or hydroxy alkylene group together with at least one other long chain alkyl group attached to the positively charged nitrogen, they are not the only compounds of the invention. The intermediates of the invention may be prepared from any of a wide variety of quaternary compounds which will react with the carboxyl group of DHICA and thereafter can be oxidatively polymerized to produce hair colorants containing a cation which will interact with hair and become attached to the hair by a cation/anion attraction of the cation for the anionic hair. It is this electronic attraction of the cation of the products of the invention for the anionic charge of the hair which renders the hair colorants of this invention semi-permanent rather than temporary as are the hair dyes of the above cited PCT patent application S.N. US93/11174 filed Nov. 17, 1993.

Accordingly, the substituents on the quaternary nitrogen atom of the quaternary reactant are not critical so long as one of them will react with DHICA to produce an ester or an amide. They are preferably, straight chain alkyl groups, but they may also be alkyloxy groups; alicyclic groups, suitably phenyl, cyclohexyl or naphthyl; cycloalkenyl such as cyclohexenyl or heterocyclic such as morpholinyl or piperidynyl.

The most preferred intermediates of the invention are those which contain at least one long chain alkyl group and at least one short chain alkyl group containing from about 1 to 6 carbon atoms, suitable methyl or ethyl. Although the invention contemplates intermediates in which all of the $R_1$, $R_2$ and $R_3$ groups are long chain, these are not preferred because they are difficult to prepare due, principally, to steric hindrance.

Suitable quaternary materials that may be used in the preparation of intermediates of this invention are set forth, generally, in the CTFA Cosmetic Ingredient Handbook (1st Ed., 1988) at pages 40–42 (quaternary ammonium compounds). The entire disclosure of this citation is incorporated herein by reference. Suitability of specific compounds may be determined by one of ordinary skill in the hair dye art by simple experimentation. They are compounds which will react with DHICA to produce intermediates which can be oxidatively polymerized to form the positively charged products of the invention having at least one counterion which is an anionic moiety, e.g., a halide or methosulfate. Using the nomenclature of the CTFA Handbook, which is widely used and accepted by chemists in the cosmetics art, illustrative cationic materials are hydroxy or amino substituted alkyl trimonium halides, alkylalkonium halides and the dialkyldimonium halides, wherein the alkyl groups have about 1 to about 22 carbons and the halide is Cl or Br. Useful quaternium compounds include for example, the quaternium series of compounds such as Quaternium 16, 22, 30, 36, 46, 78, 79, 80 and 82. Other suitable quaternary reactants will be readily apparent to the skilled artisan after the benefit of this disclosure.

It will be apparent from the foregoing that the quaternary compounds used to produce intermediates may contain a variety of functional groups both in the main chain or attached thereto.

The anion in the intermediates of this invention may be any of those normally associated with quaternary compounds. Typically they are halides, preferably chlorides or bromides.

DETAILED DESCRIPTION OF THE INVENTION

The intermediates of the invention may be formed by any of the usual methods of forming amides or esters.

For example, to form amides, DHICA may be reacted with an aminoalkyl substituted quaternary compound in an aqueous buffer at a pH of about 7 at ambient temperature in the presence of a carbodiimide such as 1-ethyl-1,3-(3-dimethylaminopropyl) carbodiimide.

Esters may be prepared for example, by reacting equimolar quantities of the reactants in an aqueous buffer at pH 7.

The intermediates of this invention may be oxidatively polymerized by a number of procedures known to those skilled in the art. The melanin like products of the invention may be produced by treatment of the selected intermediate with an oxidizing agent such as, for example, hydrogen peroxide, potassium ferricyanide, potassium permanganate or ammonium persulfate. These procedures are well known and are described for example in U.S. Pat. Nos. 5,173,083; 5,346,509; 5,273,550 and 4,804,385, the entire disclosures of which are incorporated herein by reference.

The amount of quaternized melanin like hair colorant required in the aqueous hair dye compositions of this invention whether the hair colorant is preformed or formed on the hair will vary according to factors such as the carrier used, the initial hair color of the user prior to dyeing, the desired end hair color and other factors well known to those skilled in the art. A tinctorially effective amount of hair colorant should be used. In general, the amount required is at least about 0.1%, typically from about 0.1% up to its solubility limit in the composition, but generally up to about 5.0%, and preferably from about 0.2% to about 3.0%, all concentrations being on a weight basis based on the total weight of the composition.

Skin compositions employing the products of this invention are generally less concentrated than those used as hair colorants. Typically, they will contain from about 0.01% to 10%, preferably 0.05% to 1% of at least one product of the invention dissolved, emulsified or suspended in a pharmaceutically acceptable skin vehicle which may be aqueous or non-aqueous and may comprise water, inert oils, emollients, surfactants, buffers or other additives such as those illustrated in the examples.

Although the pH of the aqueous compositions of this invention may not be so low or high as to damage skin or hair, the compositions are useful at a wide range of pH values. The optimal pH for a particular composition may vary with the hair colorant employed. In general, however, the pH of the composition will be about 3 to about 10, preferably 5 to 10.

In addition to the selected hair colorant or mixture of hair colorants of the invention, it may be desirable to include cosmetically acceptable carriers in the hair colorant compositions of this invention. Acceptable carriers vary from simple solutions or dispersions with aqueous or alcoholic solvents to complex mixtures that contain thickening or other agents. The carriers that may be used in accordance with this invention must be compatible with the selected dye.

It may also be desirable to include in the compositions of this invention adjuvants or additives that are commonly found in such compositions, in amounts effective to provide their intended function. Such adjuvants or additives include, for example, solvents, solubilizing agents, surfactants, thickening agents, alkalizing agents, chelating agents, preservatives and fragrances.

The solvents that may be used include organic solvents or solvent systems that are compatible with the other components. A number of organic solvents are known in the art that are useful for such purposes. These organic solvents include alcohols, particularly alkyl alcohols of 1–6 carbons, especially ethanol and propanol; and glycols of up to about 10 carbons, especially diethyleneglycol; monobutyl ether; carbitols and benzyl alcohol.

The thickening agents that may be used include, polyvinylpyrrolidone, gum arabic, cellulose derivatives such as methylcellulose or hydroxyethylcellulose, and inorganic thickeners such as bentonite. The solubilizing agents that may be employed include for example, ethoxylated fatty alcohols. The preservatives that may be used include: methyl and propyl paraben, 2-phenoxyethanol, DMDMH, and Kathon CG.

A special advantage of the hair colorants of this invention is that certain of them can be employed to both color and condition the hair at the same time. It is known that when long chain alkyl substituents containing certain quaternary ammonium salts are deposited on human hair, they improve combability, i.e., the relative ease with which hair can be combed, by imparting a certain lubricity to the hair as well as by providing an antistatic effect. Both of these effects combine to make the hair easier to manage so that the desired appearance of the hair can be more readily achieved. Compositions having these properties are called "hair conditioners". See, for example, A. C. Lunn and R. E. Evans, *The Electrostatic Properties of Human Hair*, J. Soc. Cosmet, Chem., 28, 549 (1977).

Products of this invention formed by oxidative polymerization of intermediates having one substituted or unsubstituted alkyl groups containing from about 12 to about 16 carbon atoms are preferred for both colorant and conditioning properties. Quaternary reactants useful for such concurrent activity include, for example, several of the Quaternium compounds mentioned above.

In another preferred aspect of the invention, the water soluble products of the invention are incorporated into a shampoo base which also contains auxiliary hair colorants to effect simultaneous coloring and cleaning of the hair. This feature of the invention is especially useful to freshen the color of previously dyed hair.

Shampoos are well known to those skilled in the art and need not be described with any particularity. In general, they are aqueous solutions containing from about 1% to about 50% by weight of a surfactant which may be cationic, anionic, non-ionic or amphoteric. Suitable surfactants include for example, behenealkonium chloride, dodecyldimonium chloride, sodium lauryl sulfate, sodium laureth sulfate, cocamidopropyl betaine and cocamidopropyl sultaine. Other useful surfactants may be identified by resort to McCutcheon's Emulsifiers and Detergents (North Amer. Edition 1987) which is incorporated herein by reference. In the compositions of this invention, the amount of surfactant is about the same as employed in conventional shampoos.

It will be appreciated that none of the various additives described above can be employed in the hair colorant compositions of the invention if they insolubilize the hair colorants of the invention at any concentration.

A further aspect of the present invention is the optional incorporation of one or more known hair color modifiers in the hair colorant compositions of the invention. These include for example, direct dyes, primary intermediates and couplers.

The concentration of hair color modifier is normally less than about 10 mg/ml, and preferably is present in the reaction medium at from about 0.01 to about 5 mg/ml, most preferably from about 0.05 to about 2 mg/ml. The amount of these components should not be so great as to cause precipitation of the hair colorants of the invention.

A wide variety of direct dyes, primary intermediates and couplers are known to the skilled artisan and can be employed in this invention.

The presently preferred primary intermediates and couplers with which they will react include:
Primary Intermediates:
p-phenylenediamine
p-aminophenol
o-aminophenol
N,N-bis(2-hydroxyethyl)-p-phenylenediamine
2,5-diaminopyridine
p-toluenediamine
Couplers:
resorcinol
m-aminophenol
α-naphthol
5-amino-o-cresol
2-methylresorcinol
4,6-di(hydroxyethoxy)-m-phenylenediamine
m-phenylenediamine Suitable direct dyes include, for example nitro dyes, azo dyes and anthraquinone dyes.

This invention also provides a process for coloring hair, which comprises applying to the hair an aqueous composition comprising a product of the invention. The compositions may be applied to the hair by conventional techniques known in the art. For example, they can be poured over the hair or applied with an applicator. The amount of time for which the dye composition must be in contact with the hair is not critical. It may vary from about 2 minutes to about one hour, but is usually from about 5 minutes to about 30 minutes.

While the presently preferred method of utilizing the products of the invention as hair colorants is to apply the preformed oxidatively polymerized melanin like products directly to the hair in aqueous compositions, it is also possible to achieve hair coloration or to treat skin by mixing an oxidant with an intermediate of the invention just prior to application or during application so that a product of the invention is formed on the hair or skin.

The invention also includes kits containing a composition of this invention. A kit may comprise one container which contains a composition including all of the various components described above. Alternatively, there may be two or more containers each containing separate components which are mixed on the hair or just prior to application to the hair or skin, or after application thereto.

The hair coloring effects achieved with the products of this invention may be evaluated utilizing the standard Hunter Tristimulus values. In the Hunter method, the parameters a and b may be positive or negative and define the chromatic condition of the hair. Thus, the more positive the a value, the greater the redness of the hair, while a negative a value indicates greenness. Similarly, positive b values indicate yellowness, while negative b values indicate blueness. The L parameter is a measure of color intensity, and has a value of 0 for absolute black to 100 for absolute white.

The following non-limiting examples are given by way of illustration only. In the examples, the formation of a cationic, positively charged pigment was shown by electrophoretic measurements in 0.05M sodium borate buffer, pH 9 at 250 Volts.

EXAMPLES

Abbreviations used: MES buffer is morpholinoethylsulphonate. EDC is 1-ethyl-3-(3-dimethylaminopropyl) carbodiimide. DHICA is 5,6-dihydroxyindole-2-carboxylic acid.

EXAMPLE 1

Reaction Product of Oxidatively Polymerized DHICA-Quaternium 22

A solution of DHICA (200 mg) in nitrogen flushed 0.1M MES buffer, pH 7 (40 ml) is treated with 1.74 ml of Quaternium 22, maintaining pH at about 7. A few mg of sodium dithionite are added, followed by 150 mg of EDC under nitrogen. After 1 h, an additional 150 mg portion of EDC is added, and the resultant mixture is left at room temperature under stirring and under nitrogen until almost all the DHICA has been consumed (about 20 h). The crude mixture is then treated with potassium ferricyanide (1 g) in 0.1M phosphate buffer (20 ml) at room temperature with continuing stirring. After 1.5 h, the solution is dialyzed against water over at least 10 h. The pigment which separates is collected by centrifugation and washed with water.

EXAMPLE 2

A 1% solution of the product of Example 1 in pH 10 buffer was prepared and applied to bleached hair for 15 minutes. Afterwards, the hair was rinsed with water and dried.

| Hunter | L | a | b |
|---|---|---|---|
| before treatment | 66.4 | 1.4 | 18.7 |
| after treatment | 42.7 | 3.2 | 14.5 |

A noticeable color and conditioning effect is imparted to the hair. The hair was shampooed, rinsed and dried. A significant amount of hair colorant remained on the hair.

| Hunter | L | a | b |
|---|---|---|---|
| shampooed hair | 51.7 | 2.0 | 16.2 |

EXAMPLE 3

A skin care composition is prepared by thoroughly mixing the following components:

| | |
|---|---|
| Product of Example 1 | 0.1% |
| Methyl cellulose | 0.5% |
| Glycerin | 2.0% |
| Ethanol | 11.0% |
| Water | 85.5% |
| Fragrance | Q.S. 100% |

When applied to the skin, the composition imparted a darker color.

EXAMPLE 4

DHICA (1.5 g) is dissolved in DMF (4 ml) and is treated with a solution of 2-aminoethyltrimethyl ammonium chloride (4 g) in water (3 ml) followed by EDC (5.45 g) solubilized in a mixture of water (2 ml) and DMF (4.5 ml). After about 1 h, 3 g of EDC is added and the mixture is stirred for additional 45 min. Sodium periodate (2 g) in water (12 ml) is then added and the mixture is allowed to stand under stirring for 20 min. Oxidation is eventually stopped with a small amount of sodium bisulfite and the resulting pigment is dialyzed against water and lyophilized.

EXAMPLE 5

A sunscreen composition is prepared by thoroughly mixing the following components:

| | |
|---|---|
| Product of Example 1 | 0.1 |
| Ethyl dihydroxypropyl PABA | 2.0 |
| Propylene Glycol | 20.0 |
| Oleth-20 | 4.7 |
| Laneth-16 | 4.7 |
| water | 68.5 |

When applied to the skin the composition afforded protection against sun rays.

What is claimed is:

1. A water soluble cationic compound obtained by oxidative polymerization of a 5,6-dihydroxindole carboxylic acid ester or amide of the formula:

$$HO\text{-}\underset{R}{\underset{|}{C_6H_2(OH)}}\text{-indole-}C(=O)\text{-}Y\text{-}(CH_2)_n\text{-}\overset{+}{N}R_1R_2R_3\ X^-$$

wherein:

Y is —O— or $$\underset{|}{\overset{H}{-N-}}$$

n is an integer from 1 to 20

R is hydrogen or alkyl having from 1 to 6 carbon atoms $R_1$, $R_2$ and $R_3$ which may be the same or different are substituted or unsubstituted alkyl groups having from 1 to 22 carbon atoms, the alkyl substituent being selected from the group consisting of halo, cyano and nitro, and X is an anion.

2. The compound of claim 1 in which n is 6 to 15.

3. The compound of claim 1 or 2 in which at least one of $R_1$, $R_2$ and $R_3$ having 1 to 22 carbon atoms and up to two of $R_1$, $R_2$ and $R_3$ having 1 to 6 carbon atoms.

4. The compound of claim 3 in which one of $R_1$, $R_2$ and $R_3$ having 12 to 16 carbon atoms and two of $R_1$, $R_2$ and $R_3$ having 1 to 6 carbon atoms.

5. A composition with a pH of from about 3 to about 10 for coloring hair or skin care containing (a) a compound obtained by oxidative polymerization of a 5,6-dihydroxindole carboxylic acid ester or amide of the formula:

$$HO\text{-}\underset{R}{\underset{|}{C_6H_2(OH)}}\text{-indole-}C(=O)\text{-}Y\text{-}(CH_2)_n\text{-}\overset{+}{N}R_1R_2R_3\ X^-$$

wherein:

Y is —O— or $$\underset{|}{\overset{H}{-N-}}$$

n is an integer from 1 to 20

R is hydrogen or alkyl having from 1 to 6 carbon atoms $R_1$, $R_2$ and $R_3$ which my be the same or different are substituted or unsubstituted alkyl groups having from 1 to 22 carbon atoms, the alkyl substituent being selected from the group consisting of halo, cyano and nitro, and X is an anion;

said compound being present in the composition in an amount effective to color hair or treat skin, and (b) a cosmetically acceptable carrier.

6. The composition of claim 5 in which n is 6 to 15.

7. The composition of claim 5 or 6 in which at least one of $R_1$, $R_2$ and $R_3$ having 1 to 22 carbon atoms and up to two of $R_1$, $R_2$ and $R_3$ having 1 to 6 carbon atoms.

8. The composition of claim 7 in which one of $R_1$, $R_2$ and $R_3$ having 12 to 16 carbon atoms and two of $R_1$, $R_2$ and $R_3$ having 1 to 6 carbon atoms.

9. A hair colorant composition of claim 5 additionally containing a surfactant in an amount of from about 1% to about 50%.

10. The composition of claim 9 in which at least one of $R_1$, $R_2$ and $R_3$ having 1 to 22 carbon atoms and up to two of $R_1$, $R_2$ and $R_3$ having 1 to 6 carbon atoms.

11. The composition of claim 10 in which one of $R_1$, $R_2$ and $R_3$ having 12 to 16 carbon atoms and two of $R_1$, $R_2$ and $R_3$ having 1 to 6 carbon atoms.

12. The composition of claim 10 in which one of $R_1$, $R_2$ and $R_3$ having 1 to 22 carbon atoms and two of $R_1$, $R_2$ and $R_3$ having 1 to 6 carbon atoms.

13. The composition of claim 10 in which one of $R_1$, $R_2$ and $R_3$ having 12 to 16 carbon atoms and two of $R_1$, $R_2$ and $R_3$ having 1 to 6 carbon atoms.

14. A compound of the formula:

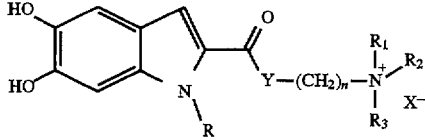

wherein:

Y is —O— or

n is an integer from 1 to 20

R is hydrogen or alkyl having from 1 to 6 carbon atoms $R_1$, $R_2$ and $R_3$ which may be the same or different are substituted or unsubstituted alkyl groups having from 1 to 22 carbon atoms, the alkyl substituent being selected from the group consisting of halo, cyano and nitro, and X is an anion.

15. A method of coloring hair which comprises contacting the hair with the product resulting from oxidatively polymerizing an intermediate of the formula:

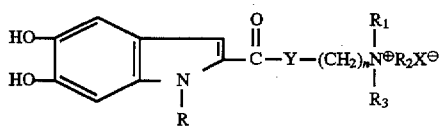

wherein:

Y is —O— or

n is an integer from 1 to 20

R is hydrogen or alkyl having from 1 to 6 carbon atoms $R_1$, $R_2$ and $R_3$ which may be the same or different are substituted or unsubstituted alkyl groups having from 1 to 22 carbon atoms the alkyl substituent being selected from the group consisting of halo, cyano, and nitro, and X is an anion.

16. The method of claim 15 wherein the intermediate is oxidatively polymerized on the hair.

17. The method of claim 15 wherein the intermediate is oxidatively polymerized prior to contacting the hair.

18. The hair colorant composition of claim 5 containing from about 0.1% to 5% of the compound obtained by oxidative polymerization.

19. The skin care composition of claim 5 containing from about 0.1% to 10% of the compound obtained by oxidative polymerization.

* * * * *